US012569676B2

(12) United States Patent
Seifert et al.

(10) Patent No.: US 12,569,676 B2
(45) Date of Patent: Mar. 10, 2026

(54) IMPLANTABLE MEDICAL SYSTEM

(71) Applicant: Medtronic, Inc., Minneapolis, MN (US)

(72) Inventors: Kevin R. Seifert, Forest Lake, MN (US); Mark T. Marshall, Cape Coral, FL (US); Teresa A. Whitman, Dayton, MN (US); Pradipta K. Das, Plymouth, MN (US); Andrew J. Ries, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 437 days.

(21) Appl. No.: 18/191,801

(22) Filed: Mar. 28, 2023

(65) Prior Publication Data

US 2023/0330412 A1 Oct. 19, 2023

Related U.S. Application Data

(60) Provisional application No. 63/362,940, filed on Apr. 13, 2022.

(51) Int. Cl.
*A61N 1/05* (2006.01)
*A61M 25/10* (2013.01)

(52) U.S. Cl.
CPC ....... *A61N 1/057* (2013.01); *A61M 25/10182* (2013.11); *A61N 2001/058* (2013.01)

(58) Field of Classification Search
CPC .............. A61N 1/057; A61N 2001/058; A61N 1/0563; A61N 1/056; A61N 1/37512;
(Continued)

(56) References Cited

U.S. PATENT DOCUMENTS 5,154,169 A 10/1992 Miyata et al.
7,801,624 B1 * 9/2010 Flannery .............. A61N 1/0573
607/116
(Continued)

FOREIGN PATENT DOCUMENTS

CN 203790445 U 8/2014
WO 2015123313 A1 8/2015
(Continued)

OTHER PUBLICATIONS

International Search Report and Written Opinion of International Application No. PCT/IB2023/053270 dated Jul. 7, 2023, 11 pp.

*Primary Examiner* — Carl H Layno
*Assistant Examiner* — Anh-Khoa N Dinh
(74) *Attorney, Agent, or Firm* — Shumaker & Sieffert, P.A.

(57) ABSTRACT

A system includes a lead with a balloon, wherein the lead defines an inflation lumen in fluid communication with the balloon. The system further includes an implantable medical device with a housing defining a fastener opening and a lead lumen. The lead lumen is configured to receive a proximal portion of the lead. The system further includes a fastener defining a fastener lumen. The fastener is configured to engage the fastener opening and the proximal portion of the lead to retain the proximal portion within the lead lumen. The fastener lumen is in fluid communication with the lead lumen and the inflation lumen, such that a pump in fluid communication with the fastener lumen inflates the balloon when the proximal portion of the lead is within the lead lumen.

20 Claims, 6 Drawing Sheets

(58) Field of Classification Search
CPC .... A61N 1/3956; A61N 1/3627; A61N 1/372;
A61N 2001/0585; A61N 1/37518; A61N
1/3752; A61N 1/0472; A61N 1/0488;
A61N 1/05; A61N 1/3754; A61N 1/39622
See application file for complete search history.

(56) References Cited

U.S. PATENT DOCUMENTS

| | | | |
|---|---|---|---|
| 8,019,437 B2 * | 9/2011 | Iaizzo .................... | A61N 1/057 |
| | | | 607/116 |
| 8,340,761 B2 | 12/2012 | Mokelke et al. | |
| 9,604,053 B2 | 3/2017 | Kaplan et al. | |
| 2004/0215139 A1 | 10/2004 | Cohen | |
| 2008/0065167 A1 * | 3/2008 | Boggs, II .......... | A61N 1/36007 |
| | | | 607/39 |
| 2013/0253347 A1 | 9/2013 | Griswold et al. | |
| 2015/0045865 A1 * | 2/2015 | Nageri ................ | A61N 1/0558 |
| | | | 607/116 |
| 2021/0290951 A1 | 9/2021 | Sanghera et al. | |

FOREIGN PATENT DOCUMENTS

| | | | |
|---|---|---|---|
| WO | 2021080765 A1 | 4/2021 | |
| WO | 2021156544 A1 | 8/2021 | |

* cited by examiner

700

702

704

INSERTING PROXIMAL PORTION OF LEAD BODY INTO LEAD LUMEN

ESTABLISHING FLUID COMMUNICATION BETWEEN PUMP AND INFLATION LUMEN VIA FASTENER LUMEN

INFLATING BALLOON OF LEAD

IMPLANTABLE MEDICAL SYSTEM

This application claims the benefit of U.S. Provisional Application Ser. No. 63/362,940, filed Apr. 13, 2022, the entire content of which is incorporated herein by reference.

TECHNICAL FIELD

This disclosure is related to an implantable medical systems, such as cardiac pacemaker systems that include a medical lead for implantation in a heart.

BACKGROUND

Some types of implantable medical devices, such as cardiac pacemakers or implantable cardioverter defibrillators, provide electrical therapy to a heart of a patient via electrodes. The electrical therapy may be delivered to the heart for pacing, cardioversion or defibrillation. The implantable medical device may include electronic circuitry to deliver the electrical therapy, where the electronic circuitry is encapsulated by a housing, such as a metal, e.g., titanium housing.

In some examples, the implantable medical devices may provide electrical therapy via implantable medical leads that include one or more electrodes. Implantable medical leads may be adapted to treat a wide variety of cardiac dysfunctions. An implantable medical lead may be navigated through vasculature of a patient to reach one or more target locations for sensing and/or therapy delivery. An electrode supported by the implantable medical lead may establish electrical communication with tissues of the heart to sense cardiac signals generated by the heart and/or deliver cardiac pacing to the patient.

SUMMARY

In general, this disclosure is directed to techniques for inflating a balloon of an implantable medical lead, e.g., during a procedure to implant the medical lead, while the lead is connected to an implantable medical device. The implantable medical lead may define an inflation lumen in fluid communication with the balloon. The inflation lumen may also be in fluid communication with a fastener lumen defined by a housing of the implantable medical device, such that a pump in fluid communication with the fastener lumen can inflate the balloon. In examples, the implantable medical device includes a polymeric enclosure rather than a metallic enclosure as is present in conventional implantable medical devices. In some instances, the implantable medical device is a pacemaker, which may be configured for more temporary use than conventional pacemakers, e.g., for a number of months rather than years.

In an example, a system comprises: an implantable medical lead comprising one or more electrodes and a balloon located at a distal portion of the implantable medical lead, and wherein the implantable medical lead defines an inflation lumen in fluid communication with the balloon; an implantable medical device configured to deliver electrical therapy via the one or more electrodes of the implantable medical lead, the implantable medical device comprising: a housing comprising a proximal end and a distal end, wherein the housing defines a fastener opening between the proximal end and the distal end and a lead lumen extending proximally from the distal end, the lead lumen configured to receive a proximal portion of the implantable medical lead; and a fastener defining a fastener lumen, wherein the fastener is configured to engage the fastener opening and the proximal portion of the implantable medical lead to retain the proximal portion within the lead lumen, and wherein the fastener lumen is in fluid communication with the lead lumen and the inflation lumen, such that a pump in fluid communication with the fastener lumen inflates the balloon when the proximal portion of the implantable medical lead is within the lead lumen.

In an example, a method comprises: inserting a proximal portion of an implantable medical lead into a lead lumen defined by a housing of an implantable medical device, wherein the implantable medical lead comprises one or more electrodes and a balloon located at a distal portion of the implantable medical lead, wherein the implantable medical lead defines an inflation lumen in fluid communication with the balloon, wherein the housing comprises a proximal end and a distal end, wherein the housing defines a fastener opening between the proximal end and the distal end, and wherein the lead lumen extends proximally from the distal end; using a fastener to engage the fastener opening and the proximal portion of the implantable lead to retain the proximal portion of the implantable medical lead within the lead lumen, wherein the fastener defines a fastener lumen, and wherein the fastener lumen is in fluid communication with the lead lumen and the inflation lumen, such that a pump in fluid communication with the fastener lumen inflates the balloon when the proximal portion of the implantable lead is within the lead lumen.

The details of one or more examples are set forth in the accompanying drawings and the description below. Other features, objects, and advantages will be apparent from the description and drawings, and from the claims.

DETAILED DESCRIPTION

In general, this disclosure is directed to techniques for inflating a balloon of an implantable medical lead while the implantable medical lead is connected to an implantable medical device. The implantable medical lead may define an inflation lumen in fluid communication with the balloon. The inflation lumen may also be in fluid communication with a fastener lumen defined by a housing of the implantable medical device, such that a pump in fluid communication with the fastener lumen can inflate the balloon. In examples, the implantable medical device includes a polymeric enclosure rather than a metallic enclosure as is present in conventional implantable medical devices. The implantable medical device may be hermetically sealed and may include a lead connector and electronics in a single structure of polymeric material that provides mechanical strength and integrity, electrical isolation, and prevents moisture and fluid ingress. In some instances, the implantable medical device is a pacemaker, which may be configured for more temporary use than conventional pacemakers, e.g., for a number of months rather than years.

Figure 1:
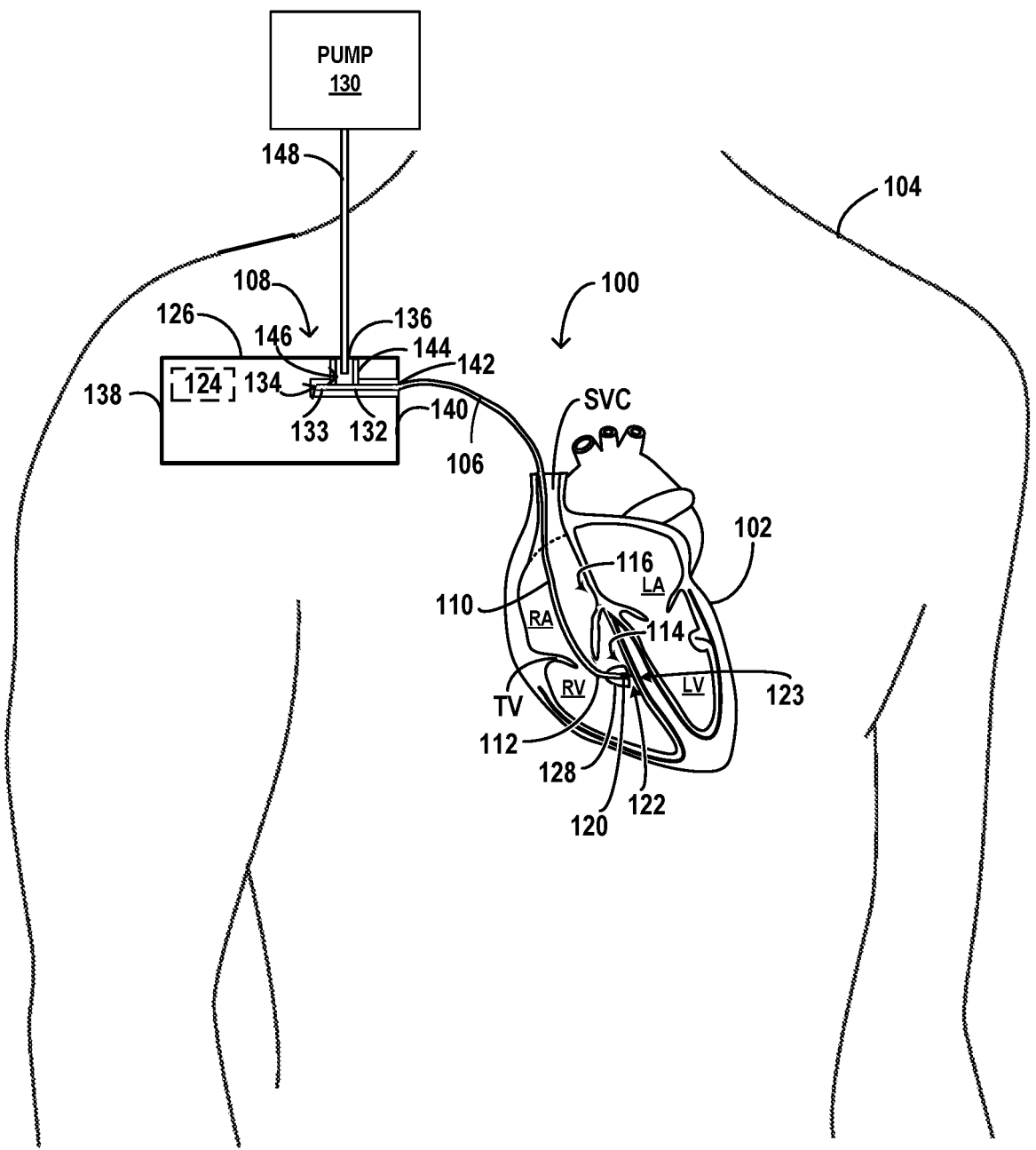
FIG. 1 is a conceptual diagram illustrating an example implantable medical system.

FIG. 1 is a conceptual diagram illustrating an example implantable medical system 100 ("system 100") configured to deliver therapy (e.g., pacing) to a heart 102 of a patient 104. System 100 includes an implantable lead 106 ("lead 106") extending from an implantable medical device 108 ("medical device 108") through vasculature of patient 104. Lead 106 includes an elongated lead body 110 with a distal portion 112 of lead body 110 ("lead body distal portion 112") generally positioned at a target site 114 within patient 104. In examples, as illustrated in FIG. 1, target site 114 is a region in the ventricular septal wall of heart 102. In examples, lead 106 may be oriented such that lead body distal portion 112 positions at another portion of heart 102. For example, lead 106 may be oriented such that lead body distal portion 112 generally positions at a target site 116 in the atrioventricular septal wall. System 100 may include additional leads coupled to medical device 108 and extending into heart 102.

Lead body distal portion 112 includes a distal end 120 ("lead distal end 120") and a fixation member 122 configured to extend distally beyond lead distal end 120. Lead body distal portion 112 mechanically supports fixation member 122. Fixation member 122 is configured to penetrate tissue of the patient 104 at or near a target sites, such as target sites 114, 116. For example, fixation member 122 may be configured to penetrate cardiac tissue of a septal wall in a RV. RA. LV, and/or LA of heart 102, or penetrate cardiac tissue in another area of heart 102. In examples, fixation member 122 is configured to remain substantially stationary with respect to lead distal end 120, such that fixation member 122 is substantially fixed in place on lead body distal portion 112. In other examples, fixation member 122 may be configured to translate relative to lead distal end 120. For example, fixation member 122 may be configured to translate distally or proximally within a lumen defined by lead body distal portion 112. Fixation member 122 may have various shapes such as helices, tines, screws, rings, and so on.

In examples, fixation member 122 mechanically supports an electrode (not shown) configured to electrically communicate with tissue when fixation member 122 positions the electrode in proximity to target sites 114, 116. In examples, the electrode is configured to provide pacing to heart 102. The electrode may be electrically connected to one or more conductors (not shown) extending through lead body 110. In some examples, the conductors are electrically connected to circuitry 124 contained within a housing 126 of medical device 108, with circuitry 124 configured to deliver therapy signals to and/or sense cardiac signals from the electrode using the conductor. Fixation member 122 may be configured to position the electrode such that the electrode conducts the electrical signals to the target tissue of heart 102, causing the cardiac muscle, e.g., of the ventricles, to depolarize and, in turn, contract at a regular interval.

System 100 includes a balloon 128 located at lead body distal portion 112. Balloon 128 defines an interior volume configured to receive an inflating medium (e.g., air, saline, or another medium), in turn resulting in inflation of balloon 128. A pump 130, such as a syringe, in fluid communication with balloon 128 may deliver the inflating medium to balloon 128. In examples, lead body 110 defines an inflation lumen fluidly coupled to the interior volume and configured such that a clinician may deliver the inflating medium to the interior volume defined by balloon 128. The inflation lumen may extend from lead body distal portion 112 to a proximal portion 132 of lead body 110 ("lead body proximal portion 132"). An exterior surface of lead body proximal portion 132 may define an opening 134 to the inflation lumen ("inflation lumen opening 134"). For example, a proximal end 133 of lead body 110 ("lead body proximal end 133") may define opening 134. The inflation lumen may extend from balloon 128 to opening 134.

Balloon 128 is configured to inflate from a deflated configuration defining an initial dimension (e.g., an initial diameter) and expand radially outward from lead body distal portion 112 to an inflated configuration defining an expanded dimension (e.g., an expanded diameter). Balloon 128 is depicted in the inflated configuration in FIG. 1. In examples, system 100 includes one or more balloons in addition to balloon 128. The additional one or more balloons may be configured similarly to or in the same manner as balloon 128.

Balloon 128 is configured to extend distally beyond lead distal end 120 when balloon 128 is in the inflated configuration. In examples, balloon 128 defines a substantially toroidal shape surrounding lead body distal portion 112 and lead distal end 120 when balloon 128 is in the inflated condition. Further, fixation member 122 (e.g., a distal end of fixation member 122) is configured to extend distal to balloon 128 when balloon 128 is in the inflated configuration. Balloon 128 may be configured to substantially surround a portion of fixation member 122 in the inflated configuration in order to, for example, minimize and/or eliminate physical interference between fixation member 122 and other anatomical structures within the patient.

A clinician may maneuver lead body 110 through the vasculature of patient 104 in order to position lead body distal portion 112 at or near a target site, such as target site 114, 116. System 100 may be configured to allow a clinician to maneuver lead body 110 through the vasculature when balloon 128 is in the inflated configuration. For example, with balloon 128 in the inflated configuration, the clinician may guide lead body distal portion 112 through the superior vena cava (SVC), into the RA, and past tricuspid valve (TV) into the RV in order to access target site 114 on the atrioventricular septal wall. The inflated balloon 128 may substantially surround a portion of fixation member 122 to maintain at least a radial displacement between fixation member 122 and anatomical structures within patient 104 (e.g., the TV, or other structures within heart 102) during the transit of lead body distal portion 112. System 100 may be configured to accommodate other pathways or techniques to reach target sites within patient 104 with balloon 128 in the inflated configuration. For example, system 100 may be configured such that the inflated configuration accommodates transit through an innominate vein, an interior vena cava (IVC), and/or another veinous pathway enroute to a chamber of heart 102.

As discussed above, balloon 128 may be configured to receive an inflating medium (e.g., air, saline, or another medium), in turn resulting in inflation of balloon 128. However, depending on the configuration of system 100, it may be impossible or impractical to deliver the inflating medium to balloon 128. For instance, the configuration of some medical devices may lack features necessary for pump 130 to be in fluid communication with the inflation lumen of lead body 110 while the medical devices are connected to a programmer or console. Alternatively, during an implantation procedure, a clinician may experience difficulty accessing the inflation lumen to establish fluid communication between pump 130 and the inflation lumen, which may undesirably increase the length of surgery.

In accordance with techniques of this disclosure, system 100 may be configured to provide access to the inflation lumen of lead body 110 via a fastener opening 136 defined by housing 126 of medical device 108. As shown in FIG. 1, housing 126 may define fastener opening 136 between a proximal end 138 of housing 126 ("housing proximal end 138") and a distal end 140 of housing 126 ("housing distal end 140"). As further shown in FIG. 1, housing 126 may define a lead lumen 142 (e.g., a bore of medical device 108), extending proximally from housing distal end 140, configured to receive lead body proximal portion 132. Fastener opening 136 may be configured to receive a fastener 144 configured to engage fastener opening 136 and lead body proximal portion 132 to retain lead body proximal portion 132 within lead lumen 142. For example, fastener 144 may define threads that engage threads defined by fastener opening 136. Additionally, when fastener 144 extends into housing 126 toward lead body proximal portion 132 (e.g., as a result of fastener 144 being tightened), fastener 144 may press against lead body proximal portion 132, thereby resisting proximal and distal movement of lead body proximal portion 132. In examples, fastener 144 includes a set screw.

Fastener 144 may define a fastener lumen 146 (e.g., a septum of medical device 108) configured to be in fluid communication with pump 130, lead lumen 142, and the inflation lumen of lead body 110. In some examples, fastener lumen 146 is directly coupled to pump 130. In other examples, fastener lumen 146 is indirectly coupled to pump 130. For instance, pump 130 may be fluidly coupled to a proximal end of a tube 148, and fastener lumen 146 may receive the distal end of tube 148. In any case, due to fastener lumen 146 being in fluid communication with pump 130 and lead lumen 142, pump 130 may deliver the inflating medium to lead lumen 142 via fastener lumen 146.

When lead body proximal portion 132 is within lead lumen 142, lead lumen 142 may be hermetically sealed, such that fluid cannot leak from housing distal end 140. However, as discussed above, an exterior surface of lead body proximal portion 132 (e.g., lead body proximal end 133) may define an opening to the inflation lumen. As a result, when lead body proximal portion 132 is within lead lumen 142, inflating medium delivered to lead lumen 142 by pump 130 via fastener lumen 146 may be forced into the inflation lumen, thereby inflating balloon 128.

By using fastener lumen 146 to inflate balloon 128 in accordance with techniques of this disclosure, balloon 128 may be inflated and deflated while medical device 108 is connected to lead 106, e.g., without requiring an additional conduit for an inflation media through medical device. The ability to implant lead 106 while connected to medical device 106 may facilitate monitoring of electrocardiogram signals via medical device 106 during implantation (e.g., to determine a location of electrode 123 at lead distal end 120 when positioning lead 106 in heart 102) without requiring a lead analyzer or other device (in addition to the medical device) to be used for that purpose. In addition, a clinician may be able to access the opening to fastener lumen 146 more easily than other openings of medical device 108, potentially decreasing the time required to establish fluid communication between pump 130 and the inflation lumen of lead body 110.

6

Figure 2:
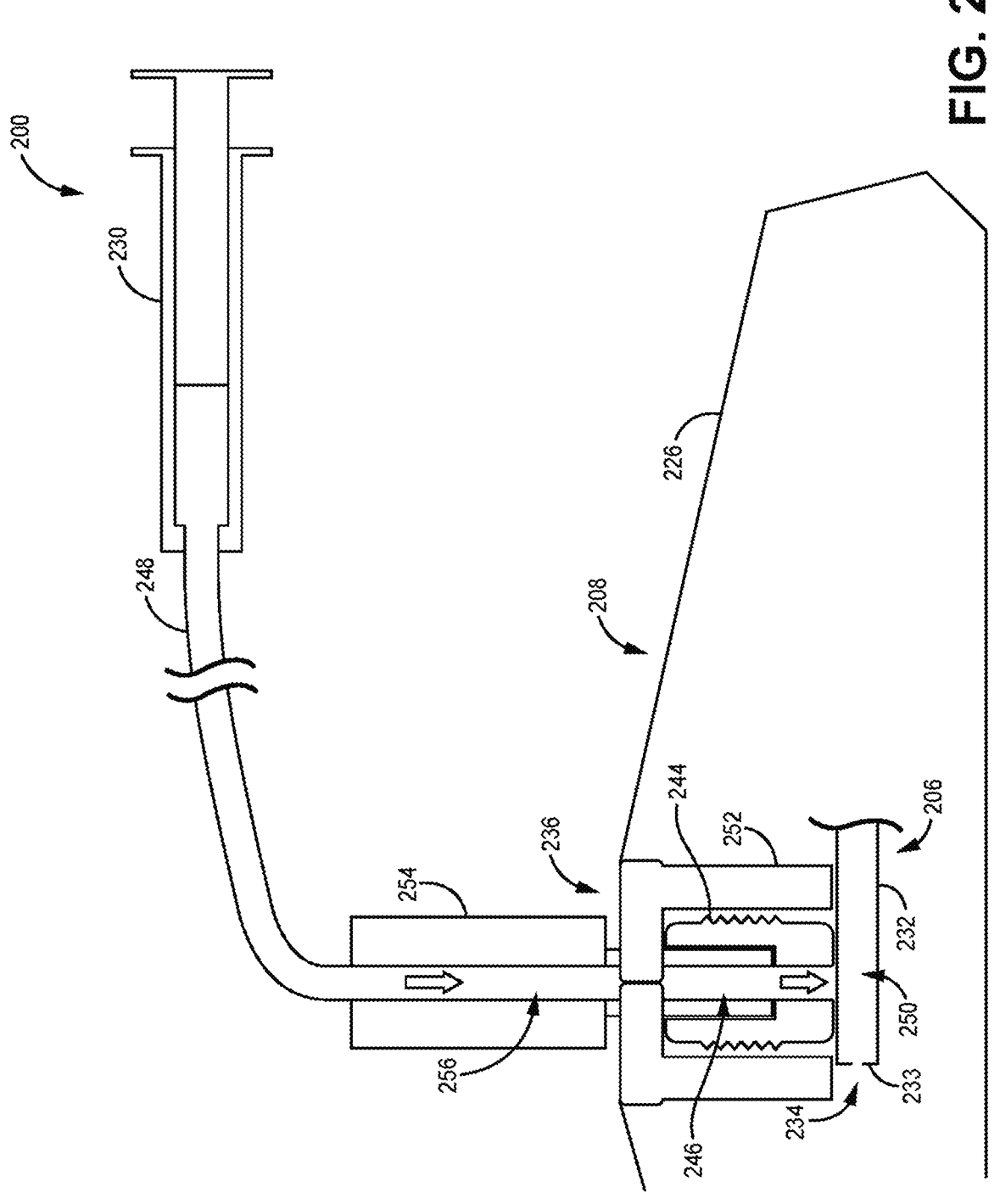
FIG. 2 is a conceptual diagram illustrating a portion of an example implantable medical system in greater detail.

FIG. 2 is a conceptual diagram of an example system 200. System 200 may be substantially similar to system 100 of FIG. 1, except for any differences described herein. For instance, system 200 may include a lead 206 of a medical device 208, a pump 230, a fastener 244, and a tube 248, each of which may be substantially similar to its counterpart described with respect to FIG. 1.

As described earlier, medical device 208 may include a housing 226. Housing 226 may contain electronic circuitry (e.g., circuitry 124), such as sensing circuitry for receiving signals from electrodes and therapy delivery circuitry configured to deliver cardiac pacing. Additionally or alternatively, the electronic circuitry may include processing circuitry and memory circuitry. In some examples, housing 226 may contain a battery. In examples, medical device 208 is a small, temporary pacemaker with at least one polymeric enclosure. Housing 226 may be at least partially formed from epoxy.

In one or more examples, housing 226 may be a preformed polymeric structure defining one or more openings. The openings are sized and configured to receive components therein. The preformed polymeric structure may be 3D printed, molded, or cast from polymeric material. In one or more examples, medical device 208 includes electrical and mechanical couplings disposed within the openings. The electrical and mechanical couplings may be for an electrical contact for an implantable lead receptacle, such as lead lumen 142, which may include electrical and/or mechanical couplings. The implantable lead receptacle allows for lead 206 to be mechanically inserted into medical device 208, and further allows for lead 206 to be mechanically and electrically coupled with medical device 208. In one or more examples, the electrical and mechanical couplings include a multi beam connector, a setscrew block and setscrew, etc.

In examples, one or more openings of housing 226 may be filled with a material (e.g., backfilled around the components within the openings). For example, polymeric material may be back filled with a material around the electronic circuits and couplings. The material may be medical adhesive, such as medical grade silicone material, epoxy, etc.

As shown in FIG. 2, a housing 226 of medical device 208 may receive a lead body proximal portion 232. In some examples, lead body proximal portion 232, e.g., a lead body proximal end 233, may define an inflation lumen opening 234 to an inflation lumen 250. Inflation lumen may be in fluid communication with fastener lumen 246 via inflation lumen opening 234. Inflation lumen opening 234 may also function as an opening for a tool, such as a stylet, a guidewire, etc.

As described earlier, fastener 244 may be configured to engage a fastener opening 236. When fastener 244 is within fastener opening 236, fastener opening 236 may be hermetically sealed, such that fluid cannot leak from fastener opening 236. In some examples, a seal 252 is positioned proximate to fastener 244 (e.g., seal 252 is at least partially positioned between fastener 244 and tube 248) and at least partially disposed within fastener opening 236. Seal 252 may be configured to resist passage of fluid (e.g., egress of inflating medium from fastener opening 236). In examples, seal 252 defines a fastener lumen 246 configured to receive fastener 244. Seal 252 may be formed from silicone or any other suitable material.

System 200 may include an implement to tighten fastener 244. For example, a torque wrench 254 may be configured to engage with and apply a torque to fastener 244. Torque wrench 254 may be configured to be in fluid communication with pump 230 and fastener lumen 246. For instance, torque wrench 254 may define a torque wrench lumen 256 configured to be in fluid communication with fastener lumen 246 when torque wrench 254 is engaged with fastener 244. In this way, pump 230 may be in fluid communication with fastener lumen 246 via torque wrench lumen 256. Additionally, torque wrench 254 may be configured to couple with tube 248.

Figure 3:
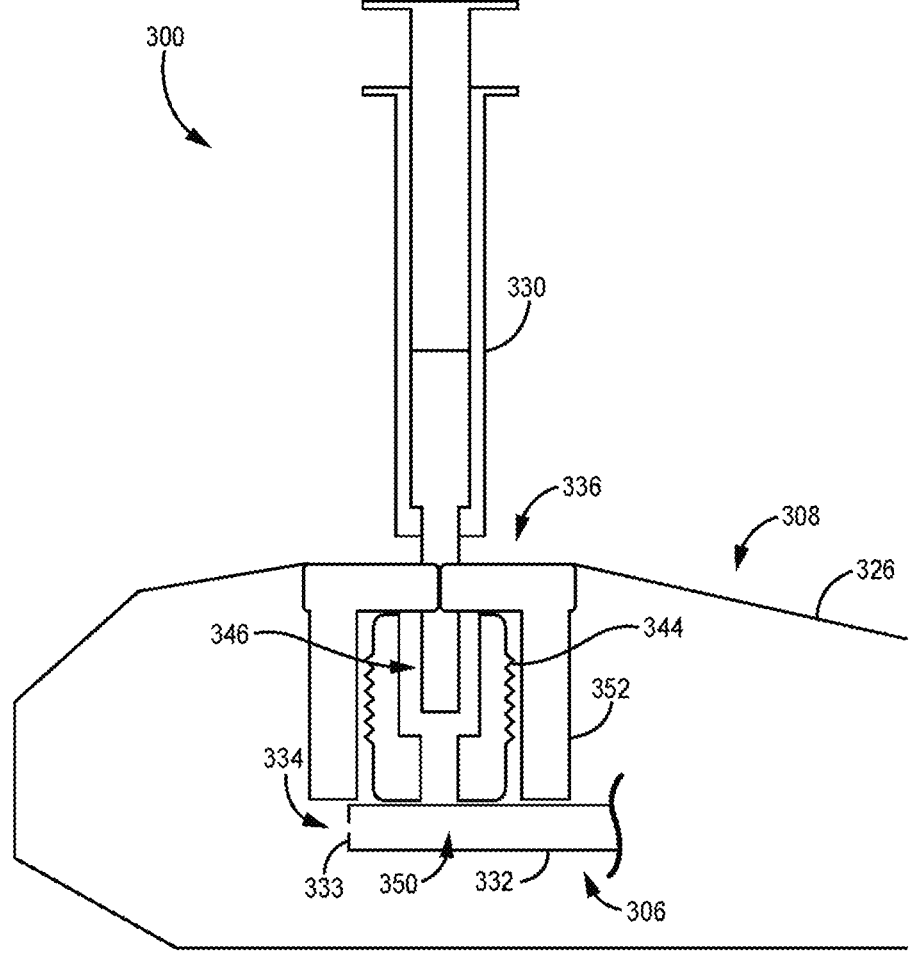
FIG. 3 is a conceptual diagram illustrating a portion of another example implantable medical system in greater detail.

FIG. 3 is a conceptual diagram of an example system 300. System 300 may be substantially similar to system 100 of FIG. 1 and/or system 200 of FIG. 2, except for any differences described herein. For instance, system 300 may include a lead 306 of a medical device 308, a pump 330, and a fastener 344 defining a fastener lumen 346, each of which may be substantially similar to its counterpart described with respect to FIG. 1 and/or FIG. 2. As shown in FIG. 3, a housing 326 of medical device 308 may receive a lead body proximal portion 332. In some examples, lead body proximal portion 332, e.g., a lead body proximal end 333, may define an inflation lumen opening 334 to an inflation lumen 350.

In contrast to system 200, system 300 may not include a tube fluidly coupling pump 330 and fastener lumen 346. Rather, as shown in FIG. 3, pump 330 may couple to a seal 352 proximate to fastener 344 and disposed at least partially within an opening 336 of housing 326, thereby establishing fluid communication between pump 330 and fastener lumen 346. As a result, inflating medium may travel from pump 330 to one or more balloons (e.g., balloon 128) via fastener lumen 346, inflation lumen opening 334, and inflation lumen 350. In the example of FIG. 3, fastener 344 may be tightened using techniques known in the art, such as a conventional torque wrench (e.g., a torque wrench that does not define a lumen). Seal 352 may be configured to resist passage of fluid.

Figure 4:
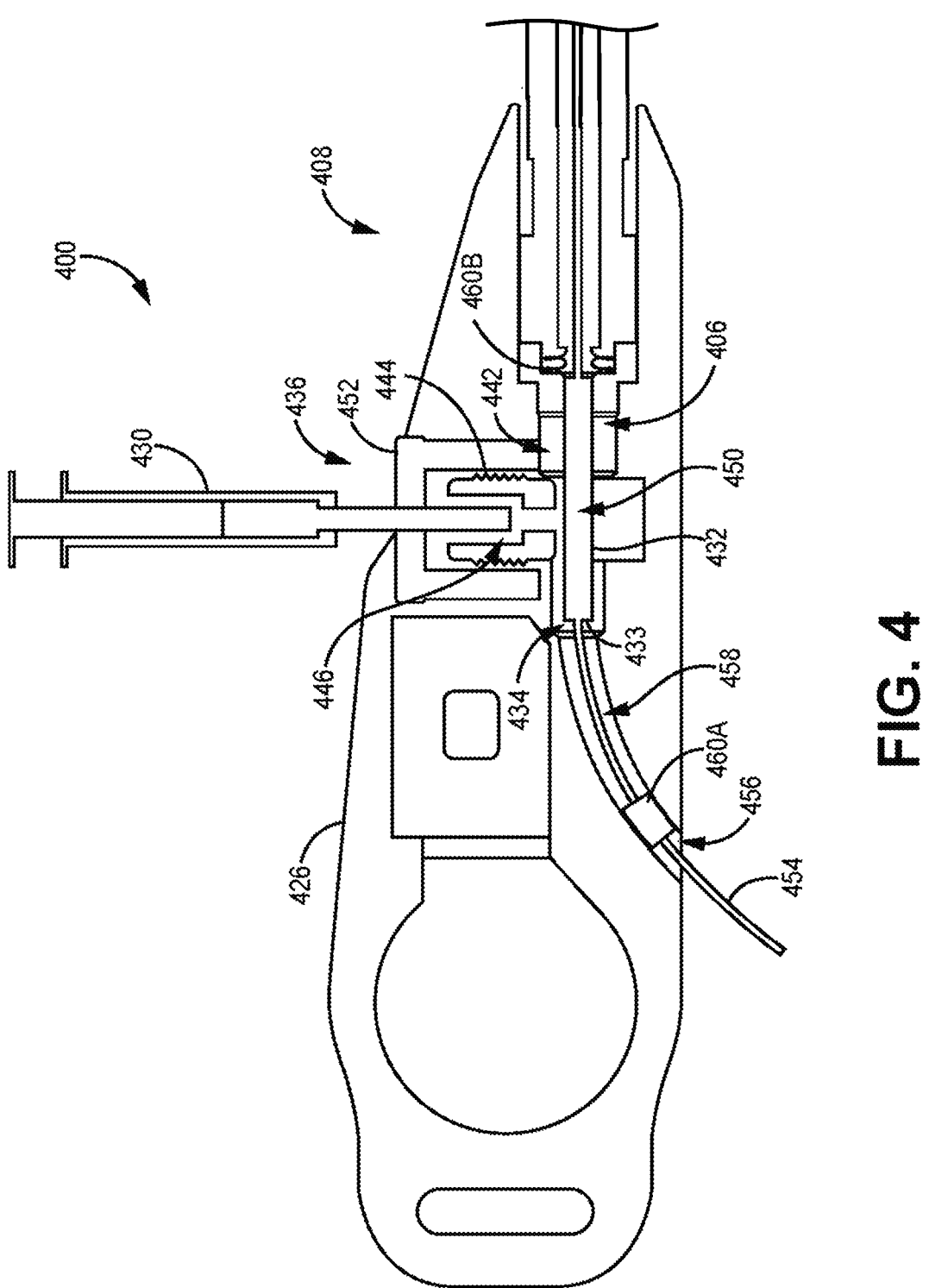
FIG. 4 is a conceptual diagram illustrating a portion of yet another example implantable medical system in greater detail.

FIG. 4 is a conceptual diagram of an example system 400. System 400 may be substantially similar to system 100 of FIG. 1, system 200 of FIG. 2, and/or system 300 of FIG. 3, except for any differences described herein. For instance, system 400 may include a lead 406 of a medical device 408, a pump 430, a fastener 444, at least partially positioned within a fastener opening 436, defining a fastener lumen 446, and a seal 452 configured to resist passage of fluid, each of which may be substantially similar to its counterpart described with respect to FIG. 1. FIG. 2, and/or FIG. 3. As shown in FIG. 4, a housing 426 of medical device 408 may receive a lead body proximal portion 432. In some examples, lead body proximal portion 432, e.g., a lead body proximal end 433, may define an inflation lumen opening 434 to an inflation lumen 450. Inflation medium may access lead lumen 442 of lead 406 in port via inflation lumen 450.

In one or more examples, system 400 may include a tool 454 configured to facilitate positioning of lead 406 during an implantation procedure. In such examples, housing 426 may define a tool opening 456 and a tool lumen 458 configured to receive tool 454. Tool lumen 458 may extend to a lead lumen 442, and a lead body proximal portion 432, and in some cases inflation lumen 450, may be configured to receive tool 454.

As shown in FIG. 4, a proximal end of lead 406 may define inflation lumen opening 434. Tool 454 may access inflation lumen 450 of lead 406 in port via tool lumen 458 and inflation lumen opening 434. Tool 454 may be inserted into inflation lumen 450 to apply a force to lead 406, thereby facilitating positioning of lead 406. Tool 454 may include a stylet, a guidewire, etc.

In some examples, medical device 408 may include a seal 460A disposed within tool lumen 458, and lead body proximal portion 432 may include a seal 460B (collectively, "seals 460"). Seals 460 may be configured to resist passage of fluid (e.g., egress of inflating medium from lead lumen 442). In this way, seals 460 may seal the portion of housing 426 in which lead body proximal portion 432 is positioned to facilitate pressurization of that portion of housing 426 (leading to inflation medium flowing into opening 434). Seal 460 may include a grommet or any other suitable structure for resisting passage of fluid.

Figure 5:
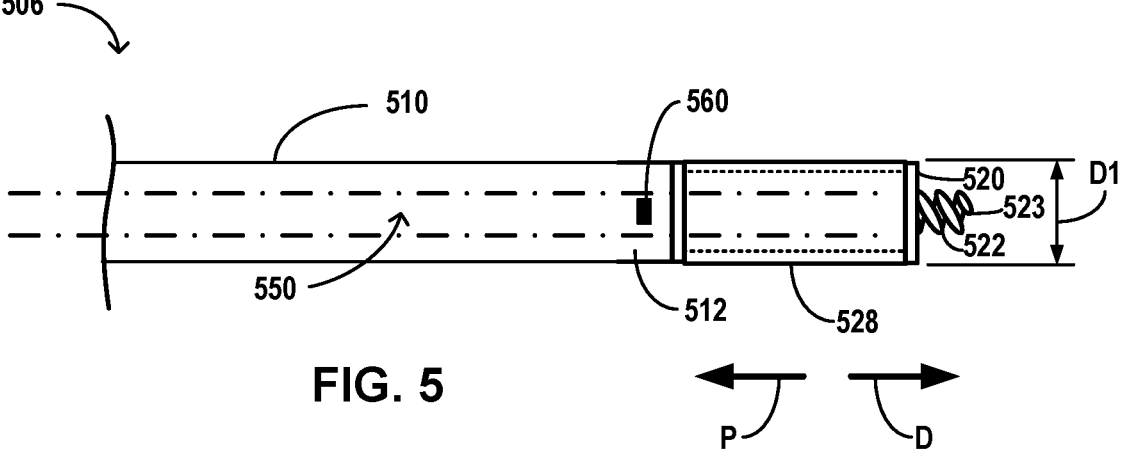
FIG. 5 is a conceptual diagram of an example implantable medical lead with a balloon in a deflated configuration.

FIG. 5 is a conceptual diagram of an example system 500. System 500 may be substantially similar to system 100 of FIG. 1, system 200 of FIG. 2, system 300 of FIG. 3, and/or system 400 of FIG. 4, except for any differences described herein. For example, system 500 includes a lead 506 with a balloon 528 located at a lead body distal portion 512. In the example of FIG. 5, system 500 may be in a configuration which may be utilized to deliver a lead body 510 to vasculature or other areas within patient 104 enroute to positioning lead body distal portion 512 in the vicinity of a target site, such as target site 114, 116. As shown in FIG. 5, an inflation lumen 550 may extend to balloon 528, such that balloon 528 and inflation lumen 550 are in fluid communication.

Balloon 528 may be affixed to lead body distal portion 512. Fixation member 522 may extend distal (e.g., in the distal direction D) to a lead distal end 520 of lead body distal portion 512. FIG. 5 illustrates system 500 with balloon 528 in the deflated configuration. Fixation member 122 may mechanically support an electrode 523 configured to electrically communicate with tissue when positioned in the vicinity of a target site within patient 104, such as target site 114, 116.

In some examples, lead body 510 is positioned within a sheath lumen of a sheath. The sheath may be, for example, an introducer sheath, such an introducer sheath configured to provide access to a jugular, innominate, and/or subclavian vein. In some examples, the sheath is a delivery catheter. The sheath may include an inner wall defining the sheath lumen and further includes a sheath opening to the sheath lumen. System 500 may be configured to translate through the sheath lumen to pass through the sheath opening when balloon 528 is in the deflated configuration.

In any case, balloon 528 may be expanded enroute to positioning lead body distal portion 512 in the vicinity of a target site within patient 104. FIG. 5 illustrates balloon 528 in the deflated configuration and defining a maximum initial dimension D1 (e.g., a diameter). System 500 may define maximum initial dimension D1, for example, to allow lead body 510 to translate through a sheath lumen and sheath opening. In examples, lead body 510 includes a marker 560 (e.g., proximal to balloon 528) configured to indicate that balloon 528 is distal to a sheath opening, such that balloon 528 is free to expand without constraint by a sheath lumen 126. Marker 560 may be configured to configured to be visible on an imaging system, such as a fluoroscope, ultrasound, or other systems configured to provide images of system 500 within patient 104.

Figure 6:
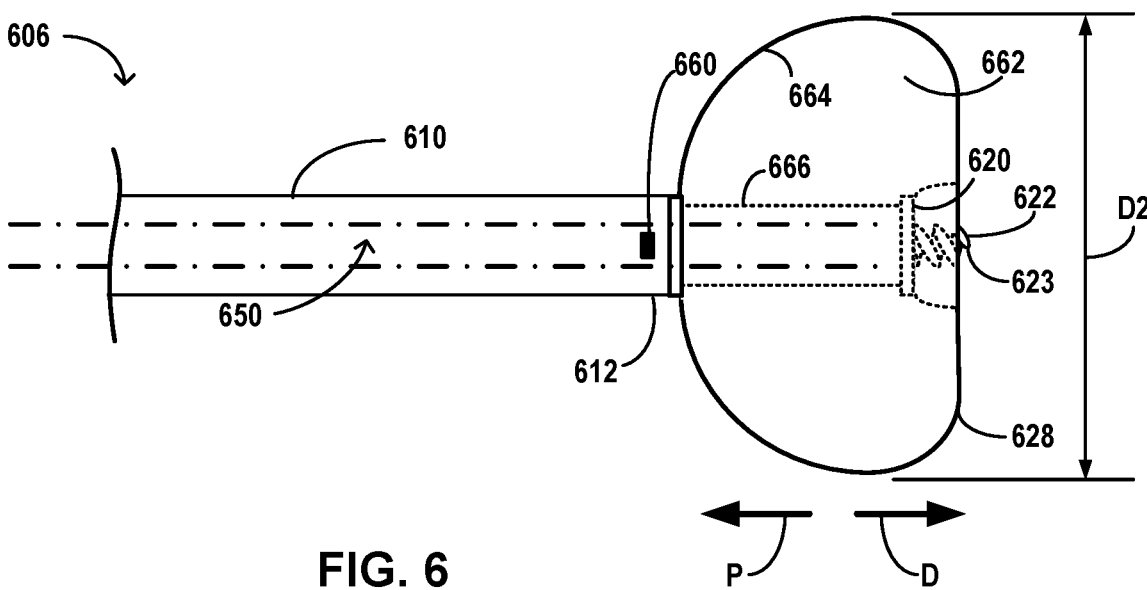
FIG. 6 is a schematic illustration of an example implantable medical lead with a balloon in an inflated configuration.

FIG. 6 is a conceptual diagram of an example system 600. System 600 may be substantially similar to system 100 of FIG. 1, system 200 of FIG. 2, system 300 of FIG. 3, system 400 of FIG. 4, and/or system 500 of FIG. 5, except for any differences described herein. For example, system 600 includes a lead 606 with a balloon 628 located at a lead body distal portion 612, a fixation member 622, an electrode 623, and a marker 660. In the example of FIG. 6, balloon 628 is in the inflated configuration.

Balloon 628 may define an interior volume 662 configured to contain an inflating medium (e.g., air, saline, or another inflating medium) to cause balloon 628 to transition from the deflated configuration of FIG. 5 to the inflated configuration depicted in FIG. 6. In examples, interior volume 662 is bound at least in part by an inner surface 664 of balloon 628 ("balloon inner surface 664") and an exterior surface 666 of lead body distal portion 612 ("distal exterior surface 666"). A lead body 610 may define an inflation lumen 650 configured to provide the inflating medium to interior volume 662. For instance, inflation lumen 650 may extend to interior volume 662, such that balloon 628 and interior volume 662 are in fluid communication.

In the inflated configuration, balloon 628 may define a maximum expanded dimension D2 (e.g., a diameter). The maximum expanded dimension D2 of the inflated configuration is greater than the maximum initial dimension D1 of the deflated configuration. In the inflated configuration, balloon 628 extends distal to a lead distal end 620, with a portion of fixation member 622 extending distal to balloon 628. Balloon 628 may substantially form a bumper circumferentially around fixation member 622. In examples, balloon 628 defines a substantially toroidal shape surrounding lead body distal portion 612 and lead distal end 620 when balloon 628 is in the inflated condition. Balloon 628 may be configured such that lead body distal portion 612 extends at least partially within a hole defined by the substantially toroidal shape. In examples, fixation member 622 is configured to extend at least partially through the hole defined by the substantially toroidal shape.

Figure 7:
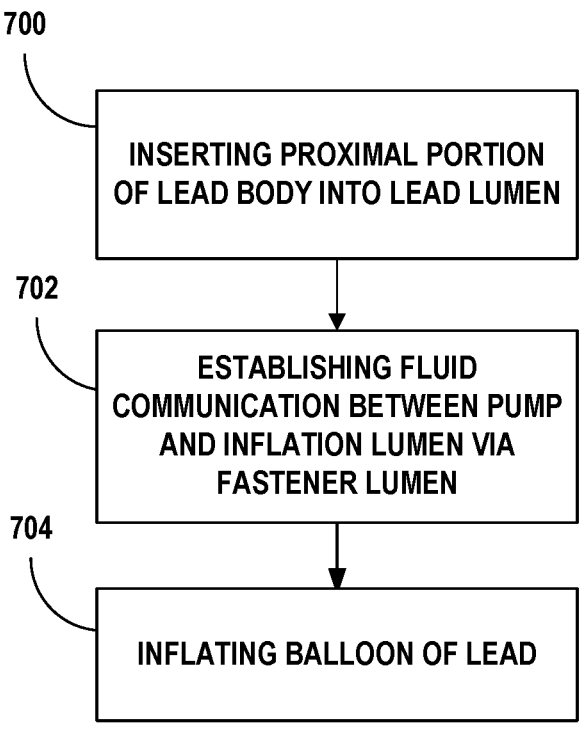
FIG. 7 illustrates an example technique for using an example implantable medical system.

FIG. 7 is a flow diagram illustrating an example technique for using an example implantable medical system. Although the technique is described mainly with reference to medical lead system 400, the technique may be applied to other medical systems in other examples.

As shown in FIG. 7, the technique includes inserting lead body proximal portion 432 into lead lumen 442 (700). Fastener opening 436 of housing 426 may receive fastener 444, and fastener 444 may retain lead body proximal portion 432 within lead lumen 442. For example, when fastener 444 extends into housing 426 toward lead body proximal portion 432 (e.g., as a result of fastener 144 being tightened), fastener 444 may press against lead body proximal portion 432, thereby resisting proximal and distal movement of lead body proximal portion 432.

The technique further includes establishing fluid communication between pump 430 and inflation lumen 450 via fastener lumen 446 (702). For example, fastener opening 436 of housing 426 may receive fastener 444, which defines fastener lumen 446, and pump 430 and inflation lumen 450 may each be in fluid communication with fastener lumen 446. Inflation lumen 450 may be in fluid communication with fastener lumen 446 via opening 434 defined by lead body proximal end 433. In some examples, fastener lumen 446 is directly coupled to pump 430. In other examples, fastener lumen 446 is indirectly coupled to pump 430. For instance, pump 430 may be fluidly coupled to a proximal end of a tube (e.g., tube 348), and fastener lumen 446 may receive the distal end of the tube. In any case, due to fastener lumen 446 being in fluid communication with pump 430 and lead lumen 442, pump 430 may deliver the inflating medium to lead lumen 442 via fastener lumen 446.

The technique further includes inflating a balloon (e.g., balloon 628), from a deflated configuration to an inflated configuration (704). The balloon may be affixed to a distal portion of a lead body (e.g., lead body distal portion 612). The technique may include expanding the balloon radially outward from an exterior surface (e.g., exterior surface 666 of lead body distal portion 612) when the balloon inflates from the deflated configuration to the inflated configuration. In examples, the technique includes positioning the lead body (e.g., lead body 610) within vasculature of the patient prior to inflating the balloon from the deflated configuration to the inflated configuration.

In examples, the technique includes issuing an inflating medium into an interior volume (e.g., interior volume 662) defined by the balloon to inflate the balloon from the deflated configuration to the inflated configuration. The technique may include issuing the inflating medium through inflation lumen 450 fluidly coupled to the interior volume. In examples, the expanded dimension is greater than at least twenty times the initial dimension.

This disclosure includes various examples, such as the following examples.

Example 1: A system includes an implantable medical lead includes a housing including a proximal end and a distal end, wherein the housing defines a fastener opening between the proximal end and the distal end and a lead lumen extending proximally from the distal end, the lead lumen configured to receive a proximal portion of the implantable medical lead; and a fastener defining a fastener lumen, wherein the fastener is configured to engage the fastener opening and the proximal portion of the lead body of the implantable medical lead to retain the proximal portion within the lead lumen, and wherein the fastener lumen is in fluid communication with the lead lumen and the inflation lumen, such that a pump in fluid communication with the fastener lumen inflates the balloon when the proximal portion of the lead body of the implantable medical lead is within the lead lumen.

Example 2: The system of example 1, wherein the housing includes a seal proximate to the fastener within the fastener opening, wherein the seal is configured to resist passage of fluid.

Example 3: The system of example 1 or 2, further including a tool configured to facilitate positioning of the implantable medical lead during an implantation procedure, wherein the inflation lumen is configured to receive the tool.

Example 4: The system of example 3, wherein the housing of the implantable medical device defines a tool lumen extending to the lead lumen and configured to receive the tool.

Example 5: The system of example 4, wherein the implantable medical device further includes a seal disposed within the tool lumen, wherein the seal is configured to resist passage of fluid.

Example 6: The system of example 5, wherein the seal includes a grommet.

Example 7: The system of any of examples 3 through 6, wherein the tool includes a stylet or a guidewire.

Example 8: The system of any of examples 1 through 7, further including a torque wrench configured to engage with and apply a torque to the fastener.

Example 9: The system of example 8, wherein the torque wrench defines a torque wrench lumen configured to be in fluid communication with the fastener lumen when the torque wrench is engaged with the fastener.

Example 10: The system of any of examples 1 through 9, wherein the implantable medical device includes a pacemaker.

Example 11: The system of any of examples 1 through 10, wherein the fastener includes a set screw.

Example 12: A method includes inserting a proximal portion of a lead body of an implantable medical lead into a lead lumen defined by a housing of an implantable medical device, wherein the implantable medical lead includes one or more electrodes and a balloon located at a distal portion of the lead body of the implantable medical lead, wherein the implantable medical lead defines an inflation lumen in fluid communication with the balloon, wherein the housing includes a proximal end and a distal end, wherein the housing defines a fastener opening between the proximal end and the distal end, and wherein the lead lumen extends proximally from the distal end; engaging the fastener opening and the proximal portion of the lead body of the implantable medical lead with a fastener to retain the proximal portion within the lead lumen, wherein the fastener defines a fastener lumen, and wherein the fastener lumen is in fluid communication with the lead lumen and the inflation lumen; and inflating the balloon with a pump in fluid communication with the fastener lumen when the proximal portion of the lead body of the implantable medical lead is within the lead lumen.

Example 13: The method of example 12, wherein the housing includes a seal proximate to the fastener within the fastener opening, wherein the seal is configured to resist passage of fluid.

Example 14: The method of example 12 or 13, further including positioning of the implantable medical lead with a tool during an implantation procedure, wherein the inflation lumen is configured to receive the tool.

Example 15: The method of example 14, wherein the housing of the implantable medical device defines a tool lumen extending to the lead lumen and configured to receive the tool.

Example 16: The method of example 15, wherein the implantable medical device further includes a seal disposed within the tool lumen, wherein the seal is configured to resist passage of fluid.

Example 17: The method of example 16, wherein the seal includes a grommet.

Example 18: The method of any of examples 14 through 17, wherein the tool includes a stylet or a guidewire.

Example 19: The method of any of examples 12 through 18, further includes engaging the fastener with a torque wrench; and applying a torque to the fastener with the torque wrench.

Example 20: The method of example 19, wherein the torque wrench defines a torque wrench lumen configured to be in fluid communication with the fastener lumen when the torque wrench is engaged with the fastener.

Example 21: The method of any of examples 12 through 20, wherein the implantable medical device includes a pacemaker.

Example 22: The method of any of examples 12 through 21, wherein the fastener includes a set screw.

Various examples of the disclosure have been described. Any combination of the described systems, operations, or functions is contemplated. These and other examples are within the scope of the following claims.

What is claimed is:

1. A system comprising:
an implantable medical lead comprising one or more electrodes and a balloon located at a distal portion of a lead body of the implantable medical lead, wherein the implantable medical lead defines an inflation lumen in fluid communication with the balloon;
an implantable medical device configured to deliver electrical therapy via the one or more electrodes of the implantable medical lead, the implantable medical device comprising:

a housing comprising a proximal end and a distal end, wherein the housing defines a fastener opening between the proximal end and the distal end and a lead lumen extending proximally from the distal end, the lead lumen configured to receive a proximal portion of the implantable medical lead; and
a fastener defining a fastener lumen,
wherein the fastener is configured to engage the fastener opening and the proximal portion of the lead body of the implantable medical lead to retain the proximal portion within the lead lumen, and
wherein the fastener lumen is in fluid communication with the lead lumen and the inflation lumen,
such that a pump in fluid communication with the fastener lumen inflates the balloon when the proximal portion of the lead body of the implantable medical lead is within the lead lumen.

2. The system of claim 1, wherein the housing comprises a seal proximate to the fastener within the fastener opening, wherein the seal is configured to resist passage of fluid.

3. The system of claim 1, further comprising a tool configured to facilitate positioning of the implantable medical lead during an implantation procedure, wherein the inflation lumen is configured to receive the tool.

4. The system of claim 3, wherein the housing of the implantable medical device defines a tool lumen extending to the lead lumen and configured to receive the tool.

5. The system of claim 4, wherein the implantable medical device further comprises a seal disposed within the tool lumen, wherein the seal is configured to resist passage of fluid.

6. The system of claim 5, wherein the seal comprises a grommet.

7. The system of claim 3, wherein the tool comprises a stylet or a guidewire.

8. The system of claim 1, further comprising a torque wrench configured to engage with and apply a torque to the fastener.

9. The system of claim 8, wherein the torque wrench defines a torque wrench lumen configured to be in fluid communication with the fastener lumen when the torque wrench is engaged with the fastener.

10. The system of claim 1, wherein the implantable medical device comprises a pacemaker.

11. The system of claim 1, wherein the fastener comprises a set screw.

12. A method comprising:
inserting a proximal portion of a lead body of an implantable medical lead into a lead lumen defined by a housing of an implantable medical device,
wherein the implantable medical lead comprises one or more electrodes and a balloon located at a distal portion of the lead body of the implantable medical lead,
wherein the implantable medical lead defines an inflation lumen in fluid communication with the balloon,
wherein the housing comprises a proximal end and a distal end,
wherein the housing defines a fastener opening between the proximal end and the distal end, and
wherein the lead lumen extends proximally from the distal end;
engaging the fastener opening and the proximal portion of the lead body of the implantable medical lead with a fastener to retain the proximal portion within the lead lumen,
wherein the fastener defines a fastener lumen, and wherein the fastener lumen is in fluid communication with the lead lumen and the inflation lumen; and inflating the balloon with a pump in fluid communication with the fastener lumen when the proximal portion of the lead body of the implantable medical lead is within the lead lumen.

13. The method of claim 12, wherein the housing comprises a seal proximate to the fastener within the fastener opening, wherein the seal is configured to resist passage of fluid.

14. The method of claim 12, further comprising positioning of the implantable medical lead with a tool during an implantation procedure, wherein the inflation lumen is configured to receive the tool.

15. The method of claim 14, wherein the housing of the implantable medical device defines a tool lumen extending to the lead lumen and configured to receive the tool.

16. The method of claim 15, wherein the implantable medical device further comprises a seal disposed within the tool lumen, wherein the seal is configured to resist passage of fluid.

17. The method of claim 16, wherein the seal comprises a grommet.

18. The method of claim 14, wherein the tool comprises a stylet or a guidewire.

19. The method of claim 12, further comprising:

engaging the fastener with a torque wrench; and applying a torque to the fastener with the torque wrench.

20. The method of claim 19, wherein the torque wrench defines a torque wrench lumen configured to be in fluid communication with the fastener lumen when the torque wrench is engaged with the fastener.

\* \* \* \* \*